United States Patent [19]

de Labbey

[11] Patent Number: 5,225,191

[45] Date of Patent: Jul. 6, 1993

[54] COSMETIC REDUCING COMPOSITIONS FOR THE PERMANENT DEFORMATION OF HAIR BASED ON AN ESTER OF THIOGLYCOLIC ACID AND AN N-($C_2$-$C_4$) ACYL CYSTEAMINE

[75] Inventor: Arnaud de Labbey, Aulnay-Sous-Bois, France

[73] Assignee: L'Oreal, Paris, France

[21] Appl. No.: 647,029

[22] Filed: Jan. 28, 1991

[30] Foreign Application Priority Data

Jan. 29, 1990 [FR] France ................................ 90 00993

[51] Int. Cl.$^5$ ........................... A61K 7/09; A61K 7/11
[52] U.S. Cl. ......................................... 424/71; 424/72; 424/70; 132/202; 132/203; 132/204
[58] Field of Search ................... 424/72, 70; 132/204, 132/205, 207, 209

[56] References Cited

FOREIGN PATENT DOCUMENTS 63-146808 6/1988 Japan .

OTHER PUBLICATIONS

Patent Abstracts of Japan, vol. 6, No. 139 (C-116)[1017], Jun. 1982, p. 9 C 116, No. 57-62217, Nemoto et al.
Patent Abstracts of Japan, vol. 12, No. 405 (C-539)[3252], Oct. 1988, p. 167 C 539, No. 63-146808, Naito et al.
French Search Report of FR 90 00993.
Zuiak, "The Science of Hair Care, Chapter 5 Permanent Waving and Hair Sraightening" pp. 183-212, 1986, Translation of JP 57-62217.

Primary Examiner—Thurman K. Page
Assistant Examiner—S. Gardner
Attorney, Agent, or Firm—Cushman, Darby & Cushman

[57] ABSTRACT

A cosmetic reducing composition for use in the permanent deformation of hair contains, as a reducing agent, a combination of an ester of thioglycolic acid and an N-($C_2$-$C_4$) acyl cysteamine, the pH of the composition being lower than 8. This composition is employed in a process for waving the hair or straightening the hair.

16 Claims, No Drawings

COSMETIC REDUCING COMPOSITIONS FOR THE PERMANENT DEFORMATION OF HAIR BASED ON AN ESTER OF THIOGLYCOLIC ACID AND AN N-(C$_2$-C$_4$) ACYL CYSTEAMINE

The present invention relates to a cosmetic reducing composition for the permanent deformation of hair based on a combination of an ester of thioglycolic acid and an N-(C$_2$-C$_4$) acyl cysteamine, as well as to a process for the permanent deformation of hair.

A classic procedure for effecting the permanent deformation of hair comprises, in a first stage, effecting the opening of the disulfide bonds of keratin using a composition containing a reducing agent (reduction stage) and then, in a second stage, preferably after having rinsed the hair, reconstituting the said disulfide bonds by applying, to the hair under tension, an oxidizing composition (oxidation stage which is also called a fixation stage) so as to impart to the hair the desired form or shape. This procedure permits indifferently to effect either a waving of the hair or a straightening of the hair.

Representative known reducing agents, employed to effect the first stage of an operation for the permanent deformation of hair, include, generally, mercaptans such as thioglycolic acid, thiolactic acid or a mixture of these acids, as well as their esters, for example, glycerol or glycol monothioglycolate.

There has also been proposed, in Japanese patent application No. 57-62221as a reducing agent, the combination of cysteamine or one of its N-alkyl derivatives and certain classic reducing agents such as thioglycolic acid, cysteine, thioglycerol and thiolactic acid, this with the view of mitigating, as much as possible the problem occasioned by the disagreeable odor of these classic reducing agents.

To this same end, it has also been proposed, in European patent application No. 0.261.387, abandoned a reducing composition containing a combination of an ester of thioglycolic acid and cysteamine or one of its salts.

It has, however, been observed that these reducing compositions, containing cysteamine, exhibited the disadvantage of giving off a disagreeable odor not necessarily during application thereof to the hair but later on when the hair was in a dampened state, and this disadvantage persisted even after repeated washings. This odor was even more accentuated with persons who experienced significant scalp perspiration.

It has now been discovered that this disadvantage can be remedied in a quite satisfactory manner by using an N-(C$_2$-C$_4$) acyl cysteamine in the reducing compositions together with an ester of thioglycolic acid.

The present invention thus relates to a cosmetic reducing composition for the permanent deformation of hair containing, as the reducing agent, an ester of thioglycolic acid and an N-(C$_2$-C$_4$) acyl cysteamine, the pH of the said composition being lower than 8.

Studies which have been carried out have also shown that by using the reducing composition according to the present invention the cosmetic condition of the hair treated is much more satisfactory and that also the composition can exhibit advantageously a greater innocuousness relative to compositions of the prior art.

According to a preferred embodiment, the ester of thioglycolic acid is glycerol monothioglycolate or ethylene glycol monothioglycolate.

Moreover, the N-(C$_2$-C$_4$) acyl cysteamine is preferably N-acetylcysteamine.

In the reducing composition according to the present invention, the ester of thioglycolic acid is generally present in an amount ranging from 5 to 30 percent by weight relative to the total weight of said composition and the concentration of the N-(C$_2$-C$_4$) acyl cysteamine preferably ranges from 0.25 to 30 percent by weight relative to the total weight of said composition.

The weight ratio between the N-(C$_2$-C$_4$) acyl cysteamine and the ester of thioglycolic acid is between 0.05 and 2.

In accordance with a preferred embodiment, the reducing composition also contains a surfactant of the nonionic, anionic, cationic or amphoteric type. Representative surfactants include alkylsulfates, alkylbenzenesulfates, alkylethersulfates, alkylsulfonates, quaternary ammonium salts, alkylbetaines, oxyethylenated alkylphenols, alkanolamides of fatty acids, esters of oxyethylenated fatty acids as well as other nonionic surface active agents of the hydroxypropylether type.

When the reducing composition contains at least one surface active agent, it is generally present in a maximum amount of 30 weight percent, but preferably between 0.5 and 10 percent by weight based on the total weight of the reducing composition.

With the view of improving the cosmetic properties of the hair or again to lessen or avoid its degradation, the reducing composition can also contain a treating agent having a cationic, anionic, nonionic or amphoteric nature.

Representative particularly preferred treating agents include principally those described in French patents No. 2.598.613 and No. 2.470.596. There can also be employed, as treating agents, volatile or non-volatile, linear or cyclic silicones, and their mixtures; polydimethylsiloxanes; quaternized polyorganosiloxanes such as those described in French patent application No. 2.535.730; polyorganosiloxanes having aminoalkyl groups modified by alkoxycarbonylalkyl groups such as those described in U.S. Pat. No. 4,749,732; polyorganosiloxanes such as the polydimethylsiloxane-polyoxyalkyl copolymer of the Dimeticone Copolyol type; a polydimethylsiloxane having stearoxy terminal groups (stearoxydimethicone); a polydimethylsiloxane-dialkylammonium acetate copolymer or a polydimethylsiloxane polyalkylbetaine copolymer described in British patent No. 2,197,352; organo polysiloxanes modified by mercapto or mercapto alkyl groups such as those described in French patent No. 1.530.369 and European patent application No. 0.295.780; as well as silanes such as stearoxytrimethylsilane.

The reducing composition can also contain other treating ingredients such as basic amino acids (such a lysine and arginine) or acids (such as glutamic acid and aspartic acid); peptides and their derivatives; swelling agents; penetrating agents or agents permitting to reinforce the efficacy of the reducing agent such as the SiO$_2$/PDMS mixture; dimethylisosorbitol; urea and its derivatives; alkyleneglycol or dialkyleneglycol alkylethers such as, for example, propyleneglycol monomethylether, dipropyleneglycol monomethylether, ethyleneglycol monoethylether and diethylene glycol monoethylether; C$_3$-C$_6$ alkanediols such as, for example, 1,2-propanediol and 1,2-butanediol; 2-pyrrolidone; 2-imidazolidinone as well as other compounds such as fatty alcohols; lanolin derivatives; active ingredients such as pantothenic acid; agents to combat hair loss;

antipellicular agents; thickening agents; suspension agents; sequesterants; opacifying agents; dyes; sunscreen agents as well as perfumes and preservatives.

The reducing composition according to the present invention is essentially provided in aqueous form and principally in the form of a thick lotion, a nonthick lotion, a cream or a gel. The pH of the reducing composition preferably ranges form 5 to 7.5 and this can be adjusted by means of a pH regulator which is either an acidifying agent selected from lactic acid, hydrochloric acid, citric acid or phosphoric acid, or an alkalizing agent selected from ammonia, mono-, di- and triethanolamine, alkaline or ammonium carbonates or bicarbonates or again by means of buffers such as, for example, mono and dipotassium phosphate and ammonium acid carbonate.

The reducing composition according to the present invention can also contain a solvent such as, for example, ethanol, propanol or isopropanol or even glycerol, at a maximum concentration of 20% relative to the total weight of the composition.

Since the esters of thioglycolic acids are not very stable in an aqueous medium it is preferable to produce the reducing composition of the present invention at the time of use by admixing the various ingredients that make up the reducing composition.

In a manner that enables the production of the reducing composition, these various ingredients are packaged in a multi-compartment kit, the ester of thioglycolic acid always being contained in one compartment thereof in an anhydrous medium.

This multi-compartment kit for packaging the reducing composition of the present invention can take several forms.

According to one form, one of said compartments of this kit contains the ester of thioglycolic acid in an anhydrous medium, preferably in glycerol and another of said compartments contains the N-($C_2$-$C_4$) acyl cysteamine in an aqueous medium.

According to another form of said multi-compartment kit, one compartment contains the ester of thioglycolic acid and the N-($C_2$-$C_4$) acyl cysteamine in an anhydrous medium, preferably in glycerol and another compartment contains an aqueous medium.

The pH regulator is generally present in the compartment containing the aqueous medium. However, in the first form of the multi-compartment kit described above, the pH regulator agent can be present in an aqueous medium in a third compartment when it is determined that this agent is incompatible with the N-($C_2$-$C_4$) acyl cysteamine.

According to these various forms of packaging the reducing composition of the present invention, cosmetic adjuvants can be present either in the aqueous phase, or in the anhydrous phase it being understood that the ester of thioglycolic acid remains in a completely anhydrous medium and that the compounds are compatible amongst themselves.

The present invention also relates to a process for waving hair wherein a reducing composition such as defined above is applied to moistened hair previously rolled up on rollers having a diameter 4 to 20 mm, the composition optionally being able to be applied in proportion of the rolling of the hair. The reducing composition is permitted to act on the hair for a period of time ranging form 5 to 60 minutes, preferably 5 to 30 minutes, at a temperature ranging from 20 to 55° C.

The hair is then thoroughly rinsed and thereafter there is applied on the rolled-up hair an oxidizing composition, so as to reform the disulfide bonds of the keratin. The oxidizing composition remains in contact with the hair for a period of time ranging from 2 to 10 minutes. After removing the rollers, the hair is thoroughly rinsed.

The oxidation composition or the oxidant is of the type currently employed and contains as the oxidizing agent, peroxides such as $H_2O_2$ or optionally urea peroxide, an alkaline bromate, a persalt or a mixture of alkaline bromate and a persalt.

The $H_2O_2$ concentration can vary from 1 to 10 volumes, but is preferably 8 volumes, the alkaline bromate concentration ranges from 1-12 percent and that of the persalt from 0.1 to 15 percent, by weight, relative to the total weight of the oxidizing composition.

The pH of the oxidizing composition can range from 2 to 7, but preferably from 4 to 6.

The $H_2O_2$ can be stabilized, for example, by phenacetin, acetalinide, mono and trisodium phosphate or by 8-hydroxy quinoline sulfate.

The oxidation can take place immediately or be delayed.

The oxidizing composition can also contain alkalizing or acidifying agents, preservatives, sequesterants, opacifiers and treating agents or active substances such as defined above for inclusion in the reducing composition.

The present invention also relates to a process for straightening the hair wherein a reducing composition according to the invention is applied to the hair which is then subject to mechanical deformation so as to fix it in its new form, by smoothing the hair with a comb having large teeth, with the back of the comb or with the hand. After a contact time of 5 to 60 minutes, in particular 5 to 30 minutes, the hair is again smoothed and is then carefully rinsed. An oxidizing or fixing composition such as defined above, is then applied to the hair and is permitted to remain in contact therewith for about 2 to 10 minutes. The hair is then thoroughly rinsed.

There is now given, as an illustration and without any limiting character, several examples of implementing the present invention.

EXAMPLE 1

In accordance with the present invention, a reducing composition for the permanent deformation of hair is prepared by proceeding in the following manner.

| Solution A is initially prepared: | |
|---|---|
| Glycerol monothioglycolate | 60 g |
| N-acetylcysteamine | 10 g |
| Glycerine, sufficient amount for | 100 g |
| Solution B is then prepared: | |
| Ammonium laurylether sulfate | 2 g |
| Perfume, sufficient amount | |
| Ammonium acid carbonate | 3 g |
| Demineralized water, sufficient amount for | 100 g |

After mixing 30 g of Solution A with 70 g of Solution B, the pH of the resulting solution is 6.9.

This composition is then applied to moistened hair, previously rolled up on rollers and is permitted to act on the hair for 20 minutes at ambient temperature. The hair is then thoroughly rinsed with water and the following oxidizing composition is applied thereto.

| | |
|---|---|
| H₂O₂ at 200 volumes | 4.8 g |
| Stabilizing agent | 0.2 g |
| Oleic alcohol oxyethylenated with 20 moles of ethylene oxide | 1.5 g |
| Citric acid, sufficient for pH = 3 | |
| Demineralized water, sufficient amount for | 100 g |

The oxidizing composition is permitted to act on the hair for 10 minutes, after which the hair is rinsed with water. The rollers are then removed.

After drying under a hood, it is observed that the hair exhibits beautiful curls with a good degree of crispness. Later, in the course of time, dampened hair exhibits no odor.

By using the operating procedures given above permanent waving of hair has been effected using the following reducing and oxidizing compositions:

EXAMPLE 2

| Reducing Composition | |
|---|---|
| Solution A | |
| Glycerol monothioglycolate | 60 g |
| Glycerine, sufficient amount for | 100 g |
| Solution B | |
| N-acetylcysteamine | 6 g |
| Oleocetyl dimethylammonium chloride | 2 g |
| Ammonium acid carbonate | 5 g |
| Perfume, sufficient amount | |
| Demineralized water, sufficient amount for | 100 g |

After mixing 30 g of Solution a with 70 g of Solution B, the ph of the resulting solution is 7.1.

| Oxidizing Composition | |
|---|---|
| H₂O₂ at 200 volumes | 4.8 g |
| Stabilizer: 8-hydroxyquinolein sulfate and phenacetin | 0.06 g |
| Citric acid, sufficient for pH = 3 | |
| Demineralized water, sufficient amount for | 100 g |

It is observed that the hair exhibits the same properties as those described above in Example 1.

EXAMPLE 3

| Reducing Composition | |
|---|---|
| Solution A | |
| Glycerol monothioglycolate | 60 g |
| N-acetylcysteamine | 12 g |
| Glycerine, sufficient amount for | 100 g |
| Solution B | |
| Lauric alcohol polyoxyethylenated with 12 moles of ethylene oxide | 3 g |
| Quaternized polyvinylpyrrolidone copolymer having a molecular weight of 1,000,000 at 20% active material, sold under the tradename "GAFQUAT 755" by GAF | 1 g (a.m.) |
| Ammonium acid carbonate | 2.7 g |
| Perfume, sufficient amount | |
| Demineralized water, sufficient amount for | 100 g |

After mixing 30 g of Solution A with 70 g of Solution B with pH of the resulting solution is 6.7.

This mixture is applied to the hair following the operating procedures of Example 1 but using a source of heat (hood at 40° C.) for 20 minutes.

The same oxidizing composition as described in Example 2 is employed.

EXAMPLE 4

This composition is identical to that described in Example 1.

| Oxidizing Composition | |
|---|---|
| Sodium bromate | 8 g |
| Triethanolamine, sufficient for pH = 7.5 | |
| Monosodium phosphate, monohydrate | 0.3 g |
| Trisodium phosphate | 0.5 g |
| Demineralized water, sufficient amount for | 100 g |

It is observed that the hair exhibits the same properties as those described in Example 1.

EXAMPLE 5

| Reducing Composition | |
|---|---|
| Solution A | |
| Glycerol monothioglycolate | 20 g |
| N-acetylcysteamine | 25 g |
| Glycerine, sufficient amount for | 100 g |
| Solution B | |
| Ammonium laurylether sulfate | 3 g |
| Ammonium acid carbonate | 1.8 g |
| Perfume, sufficient amount | |
| Demineralized water, sufficient amount for | 100 g |

After mixing 30 g of Solution a with 70 g of Solution B the pH of the resulting solution is 6.8.

Oxidizing Composition

The same oxidizing composition as described in Example 2 is employed.

It is observed that the hair exhibits the same properties as those described in Example 1.

Example 6

| Reducing Composition | |
|---|---|
| Solution A | |
| Glycerol monothioglycolate | 40 g |
| N-acetylcysteamine | 20 g |
| Glycerine, sufficient amount for | 100 g |
| Solution B | |
| Poly(hydroxypropylether non-ionic surfactant, prepared by condensation, with alkaline catalyst, of 3.5 moles of glycidol on a mixture of $C_{11}$–$C_{14}$ α-diols in accordance with the process described in French patent No. 2.091.056 | 3 g |
| Silicone cationic polymer, sold by Union Carbide under the trade name "UCAR SILICONE ALK 56", 35% active material | 1 g (a.m.) |
| Ammonium acid carbonate | 2 g |
| Demineralized water, sufficient amount for | 100 g |

After mixing 30 g of Solution A with 70 g of Solution B, the pH of the resulting solution is 6.8.

This mixture is applied to the hair following the operating procedures described in Example 1, but using a source of heat (hood at about 40° C.) for 20 minutes.

Oxidizing Composition

The same oxidizing composition as that described in Example 2 is employed.

It is observed that the hair exhibits the same properties as those described in Example 1.

Example 7

| Reducing Composition | |
| --- | --- |
| Solution A | |
| Ethylene glycol monothioglycolate | 60 g |
| N-acetylcysteamine | 10 g |
| Glycerine, sufficient amount for | 100 g |
| Solution B | |
| Ammonium laurylether sulfate | 2 g |
| Ammonium acid carbonate | 3.5 g |
| Perfume, sufficient amount | |
| Demineralized water, sufficient amount for | 100 g |

After mixing 30 g of Solution A with 70 g of Solution B, the pH of the resulting solution is 6.9.

This mixture is applied to the hair following the operating procedures described in Example 1.

Oxidizing Composition

The same oxidizing composition as that described in Example 1 is employed.

It is observed that the hair exhibits the same properties as those described in Example 1.

I claim:

1. A cosmetic reducing composition for use in the permanent deformation of hair comprising as a reducing agent from 5 to 30 percent by weight based on the total weight of said composition of a glycerol or ethylene glycol ester of thioglycolic acid and from 0.25 to 30 percent by weight based on the total weight of said composition of an N-($C_2$-$C_4$) acyl cysteamine, the pH of said composition being lower than 8 and wherein the weight ration between said N-($C_2$-$C_4$) acyl cysteamine and said ester of thioglycolic acid is between 0.05 and 2.

2. The composition of claim 1 wherein said N-($C_2$-$C_4$) acyl cysteamine is N-acetylcysteamine.

3. The composition of claim 1 which also contains at least one nonionic, anionic, cationic or amphoteric surfactant in a maximum amount of 30 weight percent based on the total weight of said composition.

4. The composition of claim 3 wherein said surfactant is present in an amount ranging from 0.5 to 10 percent by weight based on the total weight of said composition.

5. The composition of claim 1 having a pH ranging from 5 to 7.5.

6. The composition of claim 1 which contains a solvent selected from ethanol, propanol, isopropanol or glycerol, said solvent being present in a maximum amount of 20 weight percent based on the total weight of said composition.

7. A multi-compartment kit for packaging the cosmetic reducing composition of claim 1, one of said compartments containing said ester of thioglycolic acid in an anhydrous medium and another of said compartments containing said N-($C_2$-$C_4$) acyl cysteamine in an aqueous medium.

8. The multi-compartment kit of claim 7 wherein yet another of said compartments contains a pH regulating agent in an aqueous medium.

9. The multi-compartment kit of claim 7 wherein said compartment containing said N-($C_2$-$C_4$) acyl cysteamine in an aqueous medium also contains a pH regulating agent.

10. A multi-compartment kit for packaging the cosmetic reducing composition of claim 1, one of said compartments containing said ester of thioglycolic acid and said N-($C_2$-$C_4$) acyl cysteamine in an anhydrous medium and another of said compartments containing an aqueous medium.

11. The multi-compartment kit of claim 10 wherein said another compartment containing said aqueous medium also contains a pH regulating agent.

12. A process for the permanent deformation of hair comprising, in a first stage to reduce the disulfide bonds of keratin, applying to said hair a reducing composition of claim 1 and in a second stage, applying to the hair an oxidizing composition to reform the said disulfide bonds.

13. The process claim 12 for waving the hair wherein said reducing composition is applied to moistened hair rolled up on rollers having a diameter ranging from 4 to 20 mm.

14. The process of claim 12 for straightening the hair wherein subsequent to applying said reducing composition to said hair, said hair is smoothed out using a comb.

15. The process of claim 12 wherein said reducing composition is permitted to act on the hair for a period of time ranging from 5 to 60 minutes.

16. The composition of claim 1 which also includes at least one agent to improve the cosmetic properties of the hair or to lessen or avoid degradation thereof, said agent having a cationic, anionic, nonionic or amphoteric nature and being present in an amount effective to improve the cosmetic properties of the hair or to lessen or avoid degradation threreif,

* * * * *